United States Patent [19]
Kanner et al.

[11] Patent Number: 5,527,334
[45] Date of Patent: Jun. 18, 1996

[54] DISPOSABLE, RETRACTABLE LANCET

[75] Inventors: Rowland W. Kanner, Guntersville; Terry B. Kehne, Arab, both of Ala.

[73] Assignee: Ryder International Corporation, Arab, Ala.

[21] Appl. No.: 248,743

[22] Filed: May 25, 1994

[51] Int. Cl.⁶ ................................................. A61B 17/32
[52] U.S. Cl. ............................................. 606/182; 128/770
[58] Field of Search ................................ 606/181–183; 128/770

[56]  References Cited

U.S. PATENT DOCUMENTS

| | | | |
|---|---|---|---|
| 4,643,189 | 2/1987 | Mintz | 606/182 |
| 5,196,025 | 3/1993 | Ranalletta et al. | 128/770 |
| 5,314,441 | 5/1994 | Cusack et al. | 606/182 |

Primary Examiner—Stephen C. Pellegrino
Assistant Examiner—William W. Lewis
Attorney, Agent, or Firm—Trexler, Bushnell, Giangiorgi & Blackstone, Ltd.

[57]  ABSTRACT

An actuator mechanism and assembly for sequentially advancing and retracting a lancet needle includes a housing having an opening for operating projection of the needle. Two guide tracks are provided within the housing for guiding separate motions of a two-part needle holder structure propelled by a drive spring, and the needle itself is smoothly guided along one of the tracks to advance and thrust the needle into a tissue penetration position immediately followed by automatic retraction along the same highly accurate linear path.

36 Claims, 2 Drawing Sheets

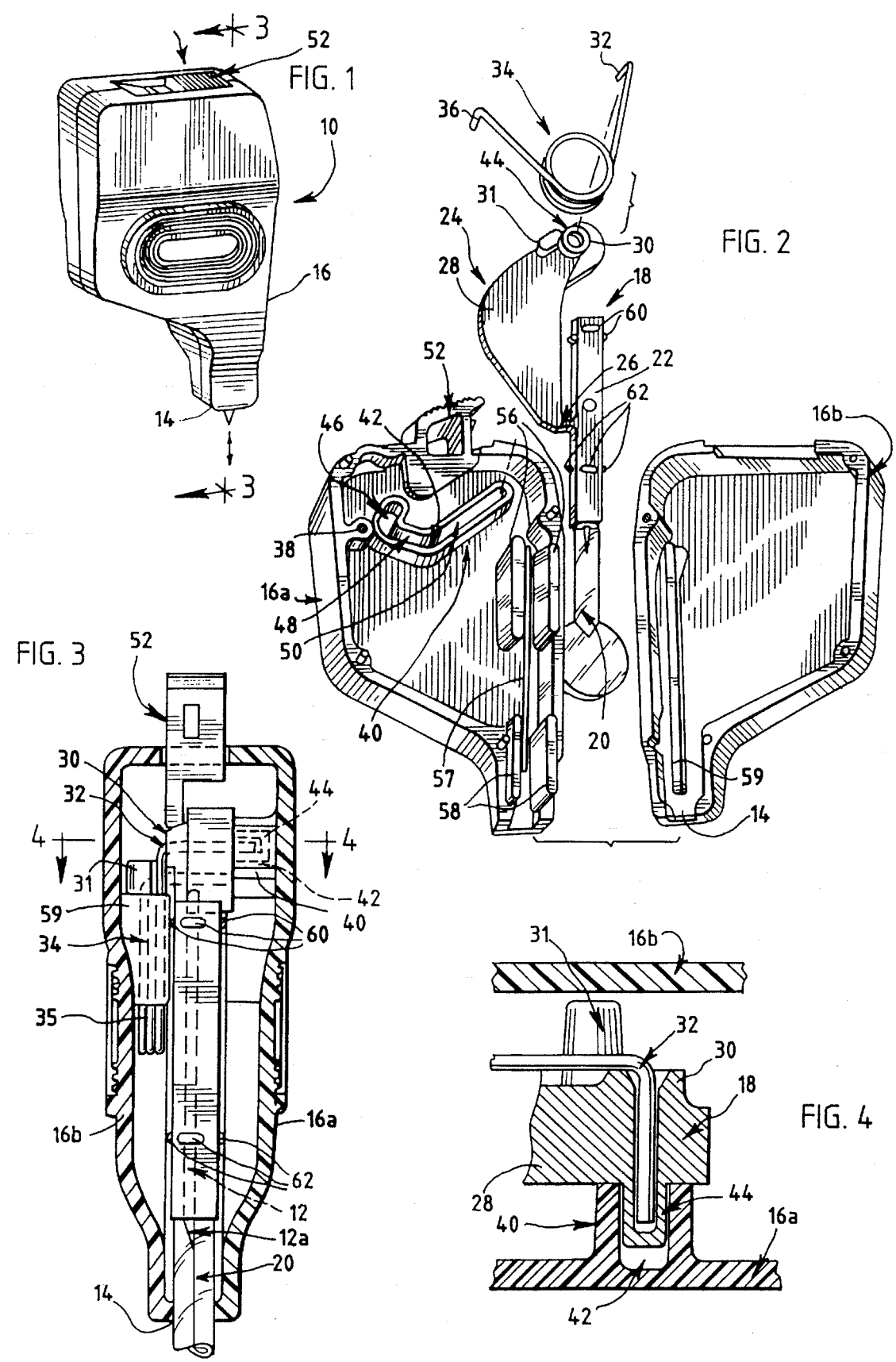

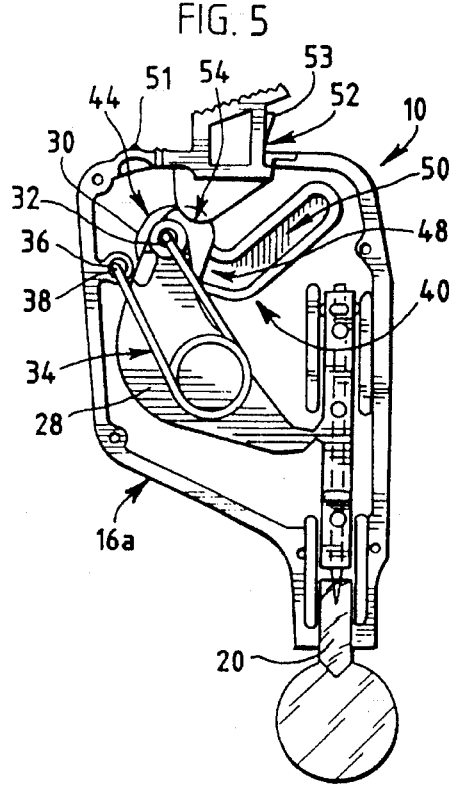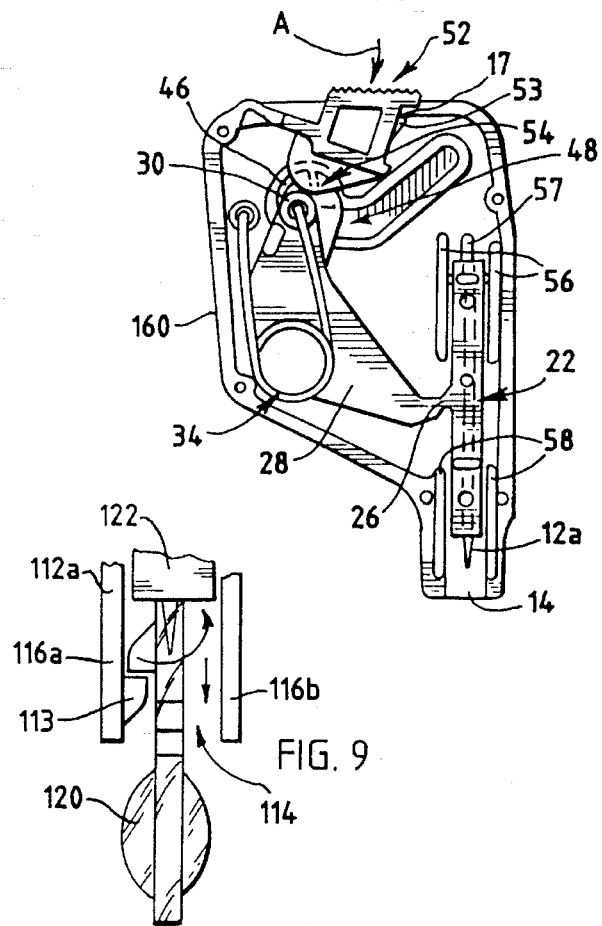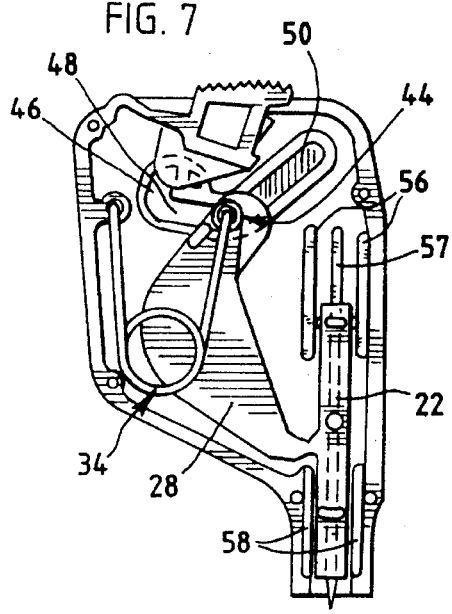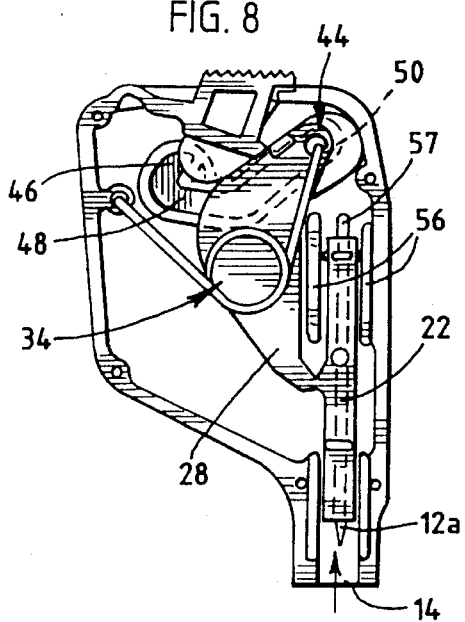

DISPOSABLE, RETRACTABLE LANCET

BACKGROUND OF THE INVENTION

This invention relates to lancet devices particularly for medical use to extract a patient's blood sample, and more particularly relates to mechanism for automatic operation of a lancet needle to initially penetrate and thereafter immediately retract the needle from the skin in a blood sampling procedure.

In order to reduce trauma to the patient during blood sampling procedures, automated finger lancet devices have been developed which eliminate the patient's view of both the skin puncture and the lancet needle or blade itself. As described for example in U.S. Pat. Nos. 4,539,988; 4,892,097; and 5,212,879, the lancet blade or needle can be housed within a small device which provides a spring-driven mechanism for thrusting and retracting the blade or needle. While such devices obstruct the patient's view, considerable patient discomfort has been experienced with lateral or rotary blade motion. Accordingly, as described for example in U.S. Pat. Nos. 4,924,879; 5,196,025; and 5,318,583, lancet devices have been developed which provide improved patient comfort by moving the lancet needle in rapid continuous thrusting and retracting motion along a linear path to eliminate lateral movement.

Lancet devices in accordance with the present invention provide improvement in construction, operation, user comfort, and disposibility as well as handling safety.

SUMMARY OF THE INVENTION

In accordance with the present invention, an actuator mechanism and assembly for sequentially advancing and retracting a lancet needle includes a housing having an opening for operating projection of the needle. Two guide tracks are provided within the housing for guiding separate motions of a two-part needle holder structure propelled by a drive spring, and the needle itself is smoothly guided along one of the tracks to advance and thrust the needle into a tissue penetration position immediately followed by automatic retraction along the same highly accurate linear path.

In a preferred embodiment, the two-part needle holder structure is preassembled within the housing and is integrally molded with a first portion carrying the needle in the reversible skin penetration motions guided by the first track, and a second, transmission linkage portion is coupled to the needle holding portion in arrangement which enables the linkage portion to move along the second guide track and induce the reversible motion of the needle holding portion along the linear guide track. The linkage portion of the needle holding structure has a cam follower with the second track providing cam guidance for the motion of the transmission linkage which is coupled by a living hinge to induce the reversible, linear needle motion. The cam track has a configuration which enables retention of a pre-cocked condition of the drive spring and transmission linkage so that only triggering of the mechanism is necessary for blood sampling operation of the device. Single use disposibility of the device is insured by permanent retraction of the needle and preventing any re-cocking capability of the pre-cocked mechanism.

BRIEF DESCRIPTION OF THE DRAWINGS

FIG. 1 is a perspective view of one embodiment of the assembled lancet actuator and device in accordance with the present invention;

FIG. 2 is an enlarged, exploded view of the assembly shown in FIG. 1;

FIG. 3 is a sectional view along a plane indicated by line 3—3 in FIG. 1;

FIG. 4 is a sectional view along a plane indicated by line 4—4 in FIG. 3;

FIGS. 5–8 are sequential views of the operating positions of the assembled actuator mechanism shown in FIGS. 1–4; and FIG. 9 is a fragmentary, diagrammatic view of a modified embodiment of needle holder construction of a lancet device in accordance with the present invention.

DETAILED DESCRIPTION OF THE PREFERRED EMBODIMENTS

Referring to FIGS. 1–3, an embodiment of a lancet actuator assembly in accordance with the present invention is generally designated by reference character 10. The illustrated embodiment of actuator 10 is designed for single-use disposibility and employs a pre-loaded, sterile needle 12 which is automatically thrusted into and immediately retracted through an operating opening 14 in a molded housing 16. In the illustrated embodiment, the metal needle 12 is encapsulated within an integrally molded, plastic lancet needle structure generally designated by reference character 18. In the assembled configuration of the actuator assembly 10, the lancet needle structure 18 includes a frangibly removable needle shield 20 which encapsulates the end 12a of the needle 12 but can be manually twisted for frangible removal from the preferred rectilinear, needle-holding body 22 of the molded structure 18 to expose the sharp, skin-penetrating end 12a of the needle 12 immediately prior to the penetration operation of the assembly 10 for blood sampling. As a result, the insert molded lancet needle 12 is fully encapsulated in thermoplastic of sufficiently high melting point so that the conventional molding temperatures sterilize the needle; the encapsulation maintains the sterility to eliminate the need for individual sterile packaging of the needle structure 18 prior to assembly in the actuator assembly 10.

Referring again to FIGS. 2 and 3, the integral needle lancet structure 18 includes both the needle holding body portion 22 and an (operating drive motion) transmission linkage portion generally designated 24 which is joined to the needle-holding portion 22 through an integral, attenuated hinge portion 26 serving as a "live hinge" for articulated operation as more fully described hereinafter. The linkage portion 24 has a generally planar, elongate main body 28 which has a transversely projecting cylindrical spring bearing 30 formed generally on the opposite end of the body 28 in relation to the integral hinge 26. The movable end 32 of a torsion drive spring 34 is inserted and secured in the spring bearing 32. The stationery end 36 of the torsion drive spring 34 is anchored by insertion into an anchoring bore 38 formed in the housing portion 16a of the split housing 16.

The housing half 16a has an integrally formed, guiding cam track wall 40 which guides travel of a cam follower pin 44 integrally formed on the main body 28 of the needle linkage portion 24 as best shown in FIG. 3. The cam follower pin 44 laterally projects from the opposite face of the main body 28 in axial alignment with the cylindrical spring bearing 30 so that the movable spring end 32 extends through the spring bearing 30 into the bored cam pin 44 for particularly balanced stability of the bearing force by the drive spring end 32 internally imposed also on the cam follower pin 44, which promotes stabilized guidance of the transmission linkage motion as hereinafter described.

As best shown in comparing FIGS. 2 and 5, the cam track wall 40 and slot 42 have a configuration including three general portions 46, 48 and 50. In the assembled actuator 10, prior to use as illustrated in FIG. 5, the cam following pin 44 is lodged against the wall of the short, initial cam slot portion 46 which is arranged at approximately right angle relative to the adjoining slot portion 48 so that the slot portion 46 serves as a pre-cocking notch leading to the slot portion 48; the cam following pin 44 is retained in the slot or notch portion 46 by the bearing force of the movable spring end 32 from the pre-wound condition of the torsion spring 34 imposing transverse, seating force of the pin 44 relative to the direction of travel necessary to release the pin 44 from the notch 46 to enter the slot portion 48.

The "pre-cocked" position of the cam following pin 44 cannot be accidentally dislodged from the slot notch 46 by pulling on the exposed twist-off needle shield 20 and is positively locked in the cocked position of FIG. 5 until the actuator 10 is deliberately triggered for blood sampling operation.

The manual trigger structure 52 is integrally molded with the housing half 16a and is pivotally joined by the attenuated hinge portion 51. The trigger structure 52 also includes a ramped barb formation 53 which will catch under the trigger edge 17 of the housing after the first inward deflection of the trigger structure 52 for blood sampling operation to retain the inwardly deflected position of the trigger structure 52 as a visual indicator of use, as shown in FIGS. 6–8, so that the user will not attempt any second blood sampling operation of the actuator 10 which will thereafter be discarded.

To operate the lancet assembly 10 for skin penetration with reference to FIGS. 6–8, the frangible, protective shield 20 is removed by twisting from the needle end 12a, and then the housing opening 14 is gently aligned against the target skin. Thereafter, the trigger structure 52 is manually deflected inwardly as indicated by arrow A so that a trigger cam projection 54 presses the end of the linkage body 28 and dislodges the cam pin 44 inwardly, against the transverse force of the spring end 32 so that the cam pin 44 is released to enter the adjoining cam slot portion 48 along which the expansion force of the spring is directed to drive the cam pin through the slot portion 48. With the downward entry of cam pin 44 into the guide slot portion 48, the same downward deflection of the linkage body 28 is transmitted through the integral hinge 26 to the needle-holding body portion 22 to initially begin downward displacement guided along a highly linear path. Upper, spaced guide ribs 56 and lower, spaced guide ribs 58 integrally formed with the housing half 16a form a linear guide track for the downward and upward displacement of the needle holding body portion 22 and needle end 12a. As the cam pin 44 is driven by the spring 34 through the medial guide slot portion 48 pulling the linkage body 28 therewith, the integral hinge 26 converts the relative pivotal motion to the needle holding body 22 inducing further linear travel thereof through the track ribs 56 and 58 thrusting the needle end 12a through the housing opening 14 with maximum extension therefrom and resulting skin penetration depth as the cam pin 44 reaches the end of the medial slot portion 48 at the entry to the succeeding slot portion 50 as shown in FIG. 7.

From the position shown in FIG. 7, continued unwinding force of the spring 34 drives the cam pin 44 through the upwardly inclined cam slot portion 50 which automatically induces, through the integral hinge 26, sequentially continuous reversal in the motion of the needle holding body 22 pulled upwardly along the same linear path through the track ribs 56 and 58, so that the needle end 12a is withdrawn from the skin penetration position of FIG. 7. In the position of FIG. 8 the cam following pin 44 reaches the end of the guide slot 50, and in the corresponding terminal position, the needle end 12a is retracted from the housing opening 14 for protection against any further danger of subsequent inadvertent skin penetration.

In the illustrated embodiment, the needle end 12a can only project from the housing opening 14 during a single, deliberately triggered blood sampling operation of the lancet assembly 10, because the entirely enclosed drive mechanism prevents any re-winding of the drive spring 34 so that after a single blood sampling operation, the lancet assembly 10 cannot be re-cocked or reused and will be discarded, effectively preventing any cross-contamination of sampled blood.

The blood sampling operation is powered by the torsion spring 34 which assures preset drive and fast penetration and retraction of the lancet needle end 12a for minimized user discomfort and precise actuation without dependence upon variable manual power. As best shown in FIGS. 2–4, the transmission linkage portion 24 has a laterally projecting spacer 31 which provides for narrow clearance with the internal wall surface of the housing portion 16b to prevent any potential twisting of the lancet needle structure 18 by the operating unwinding of the torsion spring 34. Additional stability is provided by the comparatively wide and flat linkage body portion 28 to promote smooth relatively sliding engagement of the spring coil portion 35 thereagainst during the actuator operation.

Referring again to FIGS. 2 and 3, in order to ensure the highly accurate linear path of both thrusting and retracting of the needle holding portion 22, the guide track formed by the spaced guide ribs 56 and 58 is further enclosed by an extended medial guide rib 57 in housing half 16a and the opposing guide rib 59 in housing 16b. Additionally, in order to minimize tracking friction against the guide ribs, the rectilinear needle holding portion 22 has upper and lower sets of facially projecting nibs 60 and 62.

Referring now to FIG. 9, a modified embodiment of an actuator assembly in accordance with the invention is shown in which one of the housing halves 116a or 116b can be provided with an internally projecting ledge adjacent the needle projection opening 114 and the frangibly removable needle shield 120, which encapsulates the needle end 112a within the integrally molded needle portion 122 can be provided with a small stop member 121 which abuts the ledge in the assembled and pre-cocked actuator assembly so that the shield 120 cannot be merely pulled through the opening 114, thereby encouraging only a manual twisting on the shield 120 for frangible removal thus discouraging any premature advancing motion of the needle end 112a prior to actual needle sampling operation of the actuator 10.

While a preferred embodiment of the present invention is shown and described, it is envisioned that those skilled in the art may devise various modifications and equivalents without departing from the spirit and scope of the appended claims.

The invention claimed is:

1. An actuating assembly sequentially advancing and retracting a lancet needle, comprising:

a) housing for containing a lancet needle structure therein and having an opening for projection therethrough of a needle portion of the lancet needle structure;

b) first guide track within said housing for guiding reversible motion of said needle portion to project and retract through said opening; and c) second guide track within said housing for guiding transmission motion of a linkage portion of said lancet needle structure coupled to said needle portion to induce said motion thereof guided by said first guide track, wherein said second guide track includes first and second substantially linear portions arranged in angled communication in order to guide corresponding redirection of said transmission motion therealong.

2. An actuating assembly according to claim 1, further comprising spring means for propelling said transmission motion of said linkage portion.

3. An actuating assembly according to claim 1, wherein said first guide track is arranged for guiding said reversible motion of said lancet needle along a linear path.

4. An actuating assembly according to claim 1, wherein said second track further comprises a third, release portion leading into said first track portion thereof.

5. An actuating assembly according to claim 4, wherein said first track portion is medially arranged between said third release portion and said second track portion.

6. An actuating assembly according to claim 1, in combination with said lancet needle structure including said linkage portion and said needle portion thereof being coupled to enable said transmission motion of said linkage portion through said first portion of said second track to produce said projecting motion of said needle portion through said housing opening, and thereafter continued transmission motion of said linkage portion through said second portion of said second track to produce retracting motion of said needle portion for withdrawal through said housing opening.

7. An actuating assembly according to claim 1, further comprising a trigger means for initiating said transmission motion of said linkage portion.

8. An actuating assembly according to claim 7, wherein said trigger means comprises a manually deflectable trigger member.

9. An actuating assembly according to claim 8, wherein said trigger member is engageable with said linkage portion to initiate said transmission motion thereof.

10. An actuating assembly for sequentially advancing and retracing a lancet needle, comprising:
   a) a housing for containing a lancet needle structure therein and having an opening for projection therethrough of a needle portion of the lancet needle structure;
   b) first guide track within said housing for guiding reversible motion of said needle portion to project and retract through said opening; and
   c) a second guide track within said housing for guiding transmission motion of a linkage portion of said lancet needle structure, further comprising a trigger means for initiating said transmission motion of said linkage portion, wherein said trigger means comprises a trigger member integrally molded with said housing.

11. An actuating assembly for sequentially advancing and retracing a lancet needle, comprising:
   a) a housing for containing a lancet needle structure therein having an opening for projection therethrough of a needle portion of the lancet needle structure;
   b) first guide track within said housing for guiding reversible motion of said needle portion to project and retract through said opening;
   c) second guide track within said housing for guiding transmission motion of a linkage portion of said lancet needle structure; and
   d) trigger means for initiating said transmission motion of said linkage portion, wherein said trigger means comprises a trigger member and further comprises retainer means for retaining said trigger member internal to said housing following a single operation of said trigger member to initiate said transmission motion.

12. An actuating assembly for sequentially advancing and retracing a lancet needle, comprising:
   a) a lancet needle structure including a linkage portion coupled to a needle holding portion thereof;
   b) a housing for containing a lancet needle structure therein and having an opening for projection therethrough of a needle portion of the lancet needle structure;
   c) a first guide track within said housing for reversible guiding motion of said needle portion to project and retract through said opening; and
   d) a second guide track within said housing for guiding transmission motion of linkage portion of said lancet needle structure, wherein said lancet needle is secured by insertion during molding of said needle holding portion.

13. An actuating assembly for sequentially advancing and retracing a lancet needle, comprising:
   a) a lancet needle structure including a linkage portion coupled to a needle holding portion thereof;
   b) a housing for containing said lancet needle structure therein and having an opening for projection therethrough of a needle portion carried on said needle holding portion of the lancet needle structure;
   c) a first guide track within said housing for reversible guiding motion of said needle portion to project and retract through said opening;
   d) a second aisle track within said housing for guiding transmission motion of linkage portion of said lancet needle structure; and
   e) cam means for guiding motion of said portion linkage portion along a guide cam in order to produce induced thrusting motion of said needle portion, wherein said cam means comprises a cam follower formed on said transmission linkage portion.

14. An actuating assembly according to claim 13, wherein said second guide track is arranged to enable single, continuous transmission motion of said linkage portion through said second guide track to produce both projecting and retracting portions of said reversible motion of said needle portion.

15. An actuating assembly according to claim 13, in combination with said lancet needle secured to said needle holding portion.

16. An actuating assembly according to claim 13, further comprising articulated coupling means for relatively pivot motion of said transmission linkage portion and needle holding portion.

17. An actuating assembly according to claim 13, wherein said cam follower comprises a cam element projecting from said transmission linkage portion for guiding said transmission motion.

18. An actuating assembly according to claim 17, further comprising a bearing member for anchoring of a drive spring thereon, wherein said beating member and said cam element are in substantially coaxial alignment on said transmission linkage portion.

19. An actuating assembly according to claim 18, wherein said bearing member and cam element are coaxially bored and said drive spring projects through said coaxially bored beating member and cam element for stabilized drive beating thereon.

20. An actuating assembly for sequentially advancing and retracing a lancet needle, comprising:
   a) a lancet needle structure including a linkage portion coupled to a needle holding portion thereof;
   b) a housing for containing a lancet needle structure therein and having an opening for projection therethrough of a needle portion carried on said needle holding portion of the lancet needle structure;
   c) a first guide track within said housing for reversible guiding motion of said needle portion to project and retract through said opening; and
   d) a second guide track within said housing for guiding transmission motion of linkage portion of said lancet needle structure, wherein said transmission linkage portion comprises bearing means for bearing of a drive member thereon to propel said transmission motion.

21. An actuating assembly according to claim 20, wherein said bearing means comprises mounting means for secured bearing of a drive spring thereon.

22. An actuating assembly for sequentially advancing and retracting a lancet needle, comprising:
   a) a lancet needle structure including a linkage portion coupled to a needle holding portion thereof;
   b) a housing for containing a lancet needle structure therein and having an opening for projection therethrough of a needle portion of the lancet needle structure;
   c) a first guide track within said housing for reversible guiding motion of said needle portion to project and retract through said opening; and
   d) a second guide track within said housing for guiding transmission motion of linkage portion of said lancet needle structure, further comprising a frangibly removable needle cover formed on said needle holding portion.

23. An actuating assembly according to claim 22, further comprising twisting means for requiring twisting motion of said frangible cover portion to frangibly remove said cover portion from said needle holding portion.

24. A lancet needle structure for use in sequentially advancing and retracting needle carried thereon, comprising:
   a) a needle holding portion for carrying advancement and retraction of a lancet needle;
   b) a transmission linkage portion coupled to said needle holding portion in arrangement enabling transmission motion of said linkage portion to induce thrusting motion of said needle portion; and
   c) cam means for guiding motion of said transmission linkage portion along a guide cam in order to produce said induced thrusting motion of said needle portion, wherein said lancet needle is secured by insertion during molding of said needle holding portion.

25. A lancet needle structure for use in sequentially advancing and retracting a lancet needle carried thereon, comprising:
   a) a needle holding portion for carrying advancement and retraction of a lancet needle;
   b) a transmission linkage portion coupled to said needle holding portion in arrangement enabling transmission motion of said linkage portion to induce thrusting motion of said needle portion, further comprising articulated coupling means for relatively pivotal motion of said transmission linkage portion and needle holding portion; and
   c) cam means for guiding motion of said transmission linkage portion along a guide cam in order to produce said induced thrusting motion in said needle portion.

26. A needle structure according to claim 25, in combination with said lancet needle secured to said needle holding portion.

27. A lancet needle structure for use in sequentially advancing and retracting a lancet needle carried thereon, comprising:
   a) a needle holding portion for carrying advancement and retraction of a lancet needle;
   b) a transmission linkage portion coupled to said needle holding portion in arrangement enabling transmission motion of said linkage portion to induce thrusting motion of said needle portion; and
   c) cam means for guiding motion of said transmission linkage portion along a guide cam in order to produce said induced thrusting motion of said needle portion, wherein said cam means comprises a cam follower formed on said transmission linkage portion.

28. A needle structure according to claim 27, wherein said cam follower comprises a cam element projecting from said transmission linkage portion for guiding said transmission motion.

29. A needle structure according to claim 27, further comprising a bearing member for anchoring of a drive spring thereon, wherein said bearing member and said cam element are in substantially coaxial alignment on said transmission linkage portion.

30. A needle structure according to claim 29, wherein said bearing member and cam element are coaxially bored and said drive spring projects through said coaxially bored bearing member and cam element for stabilized drive bearing thereon.

31. A lancet needle structure for use in sequentially advancing and retracting a lancet needle carried thereon, comprising:
   a) a needle holding portion for carrying advancement and retraction of a lancet needle;
   b) a transmission linkage portion coupled to said needle holding portion in arrangement enabling transmission motion of said linkage portion to induce thrusting motion of said needle portion; and
   c) cam means for guiding motion of said transmission linkage portion along a guide cam in order to produce said induced thrusting motion of said needle portion, wherein said transmission linkage portion comprises bearing means for bearing of a drive member thereon to propel said transmission motion.

32. A needle structure according to claim 31, wherein said bearing means comprises mounting means for secured bearing of a drive spring thereon.

33. A lancet needle structure for use in sequentially advancing and retracting a lancet needle carried thereon, comprising:
   a) needle holding portion for carrying advancement and retraction of a lancet needle;
   b) a transmission linkage portion coupled to said needle holding portion in arrangement enabling transmission motion of said linkage portion to induce thrusting motion of said needle portion;
   c) cam means for guiding motion of said transmission linkage portion along a guide cam in order to produce said induced thrusting motion of said needle portion; and
   d) a frangibly removable needle cover formed on said needle holding portion.

34. A needle structure according to claim 33, further comprising twisting means for requiring twisting motion of said frangible cover portion to frangibly remove said cover portion from said needle holding portion.

35. An actuating assembly for sequentially advancing and retracting a lancet needle, comprising:

a) a lancet needle structure including a linkage portion coupled to induce motion of a needle carriage portion thereof;

b) a housing for containing said lancet needle structure therein and having an opening for projection therethrough of a needle carried on said needle carriage portion;

c) a first guide track within said housing for guiding reversible motion of said needle carriage portion to project and retract the carried needle through said opening; and d) a second guide track within said housing for guiding transmission motion of said linkage portion of said lancet needle structure; wherein said second guide track comprises first and second portions arranged in communication to guide corresponding redirection of said transmission motion therealong and further comprises a third, release portion leading into said first track portion thereof.

36. An actuating assembly according to claim 35 in combination with a replaceable lancet needle carried on said needle carriage portion.

\* \* \* \* \*

UNITED STATES PATENT AND TRADEMARK OFFICE
CERTIFICATE OF CORRECTION

PATENT NO. : 5,527,334
DATED : June 18, 1996
INVENTOR(S) : Rowland W. Kanner, Terry B. Kehne It is certified that error appears in the above-indentified patent and that said Letters Patent is hereby corrected as shown below:

Column 6, Line 35 "aisle" should be --guide--

Column 6, Line 38 "portion" should be -- transmission --

Column 6, Line 62 "beating" should be --bearing --

Column 7, Line 1 "beating member" should be --bearing member --

Column 7, Lines 1-2 "beating thereon" should be -- bearing thereon --

Column 7, Line 43 " retracting needle" should be -- retracting a lancet needle--.

Signed and Sealed this

Third Day of December, 1996

Attest:

BRUCE LEHMAN

Attesting Officer

Commissioner of Patents and Trademarks